US009152829B2

(12) United States Patent
Day et al.

(10) Patent No.: US 9,152,829 B2
(45) Date of Patent: Oct. 6, 2015

(54) METHOD AND SYSTEM FOR DETERMINING INFORMATION RELATED TO A DRUG RESERVOIR USING AN ELECTRONIC SENSOR

(75) Inventors: Shane Alistair Day, Warwick (GB); Barry Yates, Kenilworth (GB); Richard James Vincent Avery, Chipping Campden (GB); David Moore, Elmesthorpe (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 171 days.

(21) Appl. No.: 13/814,491

(22) PCT Filed: Aug. 17, 2011

(86) PCT No.: PCT/EP2011/064166
§ 371 (c)(1),
(2), (4) Date: Apr. 29, 2013

(87) PCT Pub. No.: WO2012/022771
PCT Pub. Date: Feb. 23, 2012

(65) Prior Publication Data
US 2013/0221097 A1    Aug. 29, 2013

Related U.S. Application Data

(60) Provisional application No. 61/375,082, filed on Aug. 19, 2010.

(30) Foreign Application Priority Data

Oct. 26, 2010 (EP) .................................... 10188857

(51) Int. Cl.
*G06K 7/00* (2006.01)
*A61M 5/20* (2006.01)
(Continued)

(52) U.S. Cl.
CPC .. *G06K 7/00* (2013.01); *A61M 5/20* (2013.01); *A61M 15/0065* (2013.01);
(Continued)

(58) Field of Classification Search
CPC ............. G06K 7/00; G06K 9/00; G06F 19/34
USPC ................... 235/454, 435, 479, 486; 604/404
See application file for complete search history.

(56) References Cited

U.S. PATENT DOCUMENTS 7,331,339 B2 *  2/2008  Smith et al. .............. 128/200.14
2003/0006209 A1  1/2003  Stefen et al.
(Continued)

FOREIGN PATENT DOCUMENTS

EP     1776975        4/2007
WO   03/047657       6/2003
(Continued)

OTHER PUBLICATIONS

International Search Report for Int. App. No. PCT/EP2011/064166, completed Aug. 20, 2012.

*Primary Examiner* — Seung Lee
(74) *Attorney, Agent, or Firm* — McDonnell Boehnen Hulbert & Berghoff LLP

(57) ABSTRACT

A medical delivery device may include at least one electronic sensor and a decoding module. The at least one electronic sensor and the decoding module are configured to (i) identify a coding feature of a drug reservoir inserted in the medical delivery device and (ii) determine information related to the drug reservoir based on the identified coding feature.

16 Claims, 8 Drawing Sheets

(51) Int. Cl.
  *A61M 15/00* (2006.01)
  *A61M 39/16* (2006.01)
  *A61J 1/06* (2006.01)
  *A61M 5/142* (2006.01)
  *A61M 5/145* (2006.01)
  *A61M 5/172* (2006.01)
  *A61M 5/315* (2006.01)
  *A61M 37/00* (2006.01)
  *A61M 5/24* (2006.01)
  *A61M 39/10* (2006.01)

(52) U.S. Cl.
  CPC .................. *A61M 39/16* (2013.01); *A61J 1/06* (2013.01); *A61J 2205/40* (2013.01); *A61M 5/1452* (2013.01); *A61M 5/14244* (2013.01); *A61M 5/1723* (2013.01); *A61M 5/31543* (2013.01); *A61M 5/31546* (2013.01); *A61M 37/00* (2013.01); *A61M 2005/2407* (2013.01); *A61M 2005/2496* (2013.01); *A61M 2005/3154* (2013.01); *A61M 2039/1022* (2013.01); *A61M 2039/1077* (2013.01); *A61M 2039/167* (2013.01); *A61M 2205/14* (2013.01); *A61M 2205/276* (2013.01); *A61M 2205/6018* (2013.01); *A61M 2205/6027* (2013.01); *A61M 2205/6036* (2013.01); *A61M 2205/6054* (2013.01); *A61M 2205/6063* (2013.01); *A61M 2205/6072* (2013.01); *A61M 2205/6081* (2013.01)

(56) References Cited

U.S. PATENT DOCUMENTS

| 2005/0107899 | A1  | 5/2005  | Steffen                |         |
|--------------|-----|---------|------------------------|---------|
| 2006/0243804 | A1* | 11/2006 | Christoffersen et al.  | 235/454 |
| 2012/0101470 | A1* | 4/2012  | Rasmussen et al.       | 604/404 |

FOREIGN PATENT DOCUMENTS

| WO | 2005/077441 | 8/2005 |
| WO | 2009/015933 | 2/2009 |
| WO | 2010/092156 | 8/2010 |

* cited by examiner

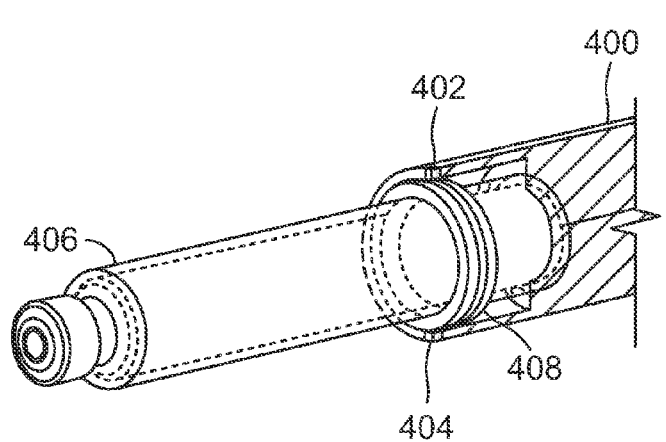
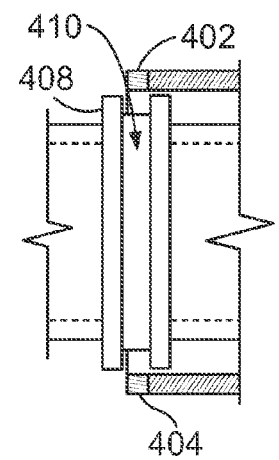
FIG. 4A              FIG. 4B
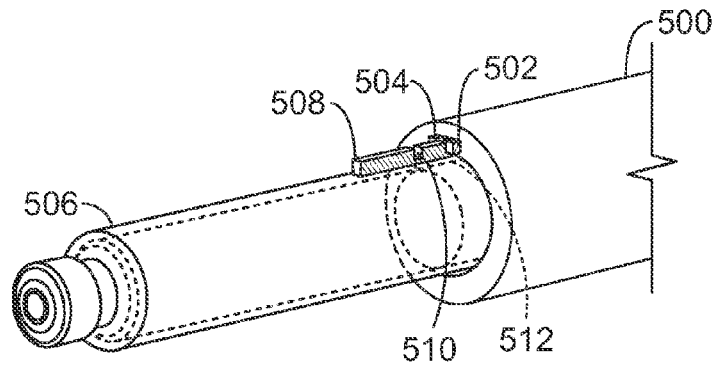
FIG. 5A
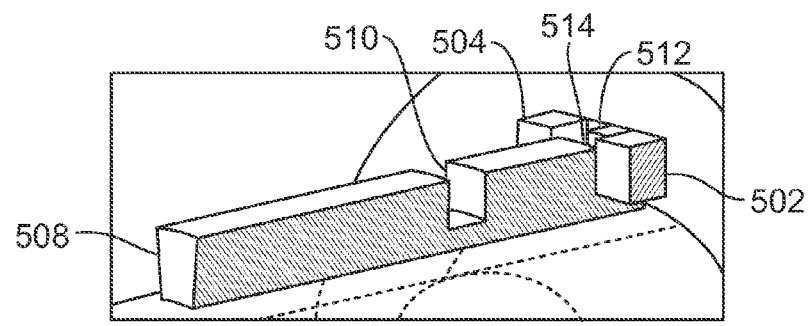
FIG. 5B

METHOD AND SYSTEM FOR DETERMINING INFORMATION RELATED TO A DRUG RESERVOIR USING AN ELECTRONIC SENSOR

CROSS REFERENCE TO RELATED APPLICATIONS

The present application is a U.S. National Phase Application pursuant to 35 U.S.C. §371, of International Application No. PCT/EP2011/064166, filed Aug. 17, 2011, which claims priority to U.S. Provisional Patent Application No. 61/375,082, filed Aug. 19, 2010, and European Patent Application No. 10188857.6, filed Oct. 26, 2010. The entire disclosure contents of these applications are herewith incorporated by reference into the present application.

FIELD OF INVENTION

Specific embodiments of the present disclosure relate to a method and system for determining information related to a drug reservoir, particularly a drug reservoir containing a medicament. As just one example, such medicament reservoirs may comprise an ampoule, a cartridge, or a vial and may be used with a medical delivery device. Such exemplary medical delivery devices could comprise a syringe, a pen type syringe, a pump, or other similar device that requires a reservoir containing at least one medicament.

BACKGROUND

The present disclosure is generally directed to reservoirs, particularly reservoirs containing a medicament. More particularly, the present disclosure is generally directed to determining information related to a drug reservoir, which may help to ensure that a delivery device can only be used with a drug reservoir for which it is intended. As just one example, such medicament reservoirs may comprise an ampoule, a cartridge, a vial, or a pouch, and may be used with a medical delivery device. Exemplary medical delivery devices include, but are not limited to syringes, pen type injection syringes, credit-card-shaped injection devices, pumps, inhalers, or other similar injection or infusing devices that require at least one reservoir containing at least one medicament.

Medicament reservoirs such as ampoules, cartridges, or vials are generally known. Such reservoirs are especially used for medicaments that may be self administered by a patient. For example, with respect to insulin, a patient suffering from diabetes may require a certain amount of insulin to either be injected via a pen type injection syringe or infused via a pump. With respect to certain known reusable pen type drug delivery devices, a patient may load a cartridge containing the insulin into a proximal end of a cartridge holder. After the cartridge has been correctly loaded, the user may then be called upon to select a dose of medicament. Multiple doses may be dosed from the cartridge. Where the drug delivery device comprises a reusable device, once the cartridge is empty, the cartridge holder may be disconnected from the drug delivery device and the empty cartridge may be removed and replaced with a new cartridge. Most suppliers of such cartridges recommend that the user may dispose of the empty cartridges properly. Where the drug delivery device comprises a disposable device, once the cartridge is empty, the user may be recommended to dispose of the entire device.

Such known self administration systems requiring the removal and reloading of empty cartridges have certain limitations. For example, in certain generally known systems, a user may simply load a new cartridge into the delivery system without the drug delivery device or without the cartridge having any mechanism of preventing cross use of an incorrect cartridge. That is, the drug delivery device does not have a mechanism for determining whether the medicament contained in the cartridge is indeed the correct type of medicament to be administered by the patient. Alternatively, certain known drug delivery devices do not present a mechanism for determining whether the correct type of medicament within the cartridge should be used with that particular drug delivery system. This potential problem could be exacerbated given that certain elderly patients, such as those suffering from diabetes, may have limited manual dexterity. Identifying an incorrect medicament is quite important, since the administration of a potentially incorrect dose of a medicament such as a short-acting insulin in lieu of a long-insulin could result in injury or even death.

Some drug delivery devices or systems may use a color coding scheme to assist a user or care giver in selecting the correct cartridge to be used with a drug delivery device. However, such color coding schemes pose challenges to certain users, especially those users suffering from poor eyesight or color blindness: a situation that can be quite prevalent in patients suffering from diabetes.

Another concern that may arise with such disposable cartridges is that these cartridges are manufactured in essentially standard sizes and manufactured to comply with certain recognized local and international standards. Consequently, such cartridges are typically supplied in standard sized cartridges (e.g. 3, ml cartridges). Therefore, there may be a variety of cartridges supplied by a number of different suppliers and containing a different medicament but fitting a single drug delivery device. As just one example, a first cartridge containing a first medicament from a first supplier may fit a medical delivery device provided by a second supplier. As such, a user might be able to load and then dispense an incorrect medicament (such as a rapid or basal type of insulin) into a drug delivery device without being aware that the medical delivery device was perhaps neither designed nor intended to be used with such a cartridge.

As such, there is a growing desire from users, health care providers, care givers, regulatory entities, and medical device suppliers to reduce the potential risk of a user loading an incorrect drug type into a drug delivery device. There is also, therefore, a desire to reduce the risk of dispensing an incorrect medicament (or the wrong concentration of the medicament) from such a drug delivery device.

One problem to be solved by the present invention is to provide a medical delivery device and a method where the safety of the user is increased.

SUMMARY

One aspect relates to a medical delivery device. The medical delivery device may include at least one electronic sensor. The medical delivery device may include a decoding module. The at least one electronic sensor and the decoding module may be configured to identify a coding feature. The coding feature may be a feature of a drug reservoir inserted in the medical delivery device. Additionally, the at least one electronic sensor and the decoding module may be configured to determine information related to the drug reservoir based on the identified coding feature.

According to an embodiment, the electronic sensor comprises the decoding module. The decoding module may comprise a processor. The decoding module may comprise a data storage. The data storage may comprise instructions executable by the processor to carry out the step of determining information related to the drug reservoir based on the identified coding feature.

According to an embodiment, the medical delivery device comprises a drug reservoir holder. The drug reservoir holder may be capable of receiving the drug reservoir. The at least one electronic sensor may be located on the drug reservoir holder, preferably on an inner wall of the drug reservoir holder.

According to an embodiment, the medical delivery device comprises a drug reservoir holder. The medical delivery device may comprise a dose setting mechanism. The drug reservoir holder may be permanently or releasably attachable to the dose setting mechanism. The at least one electronic sensor may be located on an inner wall of the dose setting mechanism.

According to an embodiment, the at least one electronic sensor comprises a plurality of electronic sensors. Each electronic sensor of the plurality may identify a respective element of the coding feature.

In an example, the at least one electronic sensor may include a sensor selected from the group consisting of an optical sensor, a photodiode, a scanner, a laser, a capacitive sensor, a Hall sensor, a switch, and an electrical contact. Further, the coding feature may be a coding feature selected from the group consisting of a bar code, a protrusion, an indentation, a color, a light-emitting coding feature, a magnet, and an electrical contact. The coding feature may serve to indicate information about the drug reservoir, such as the type of drug the reservoir holds. The above-mentioned sensors and coding features are intended as examples only, and other sensors and coding features are possible as well.

According to an embodiment, the at least one electronic sensor comprises a zebra-strip sensor.

According to an embodiment, the coding feature comprises a plurality of coding elements.

According to an embodiment, the medical delivery device further comprises a light source, e.g. an LED. Light from the light source may interact with the sensor. The coding feature may guide from the light source to the sensor. The coding feature may allow light from the light source to travel to the at least one sensor.

According to an embodiment, the coding feature is a mechanical coding feature, e.g a protrusion and/or and indentation. The mechanical coding feature may comprise a plurality of geometric features. The coding feature may comprise at least one protrusion around a ring. The ring may wrap around the drug reservoir.

A further aspect relates to a medical delivery device. The medical delivery device may comprise a drug reservoir. The drug reservoir may be configured to be at least partially inserted into the medical delivery device. The medical delivery device may comprise at least one coding feature. The at least one coding feature provided on the drug reservoir. The medical delivery device may comprise at least one electronic sensor. The at least one electronic sensor may be configured to identify the at least one coding feature.

According to an embodiment, a location of the at least one coding feature represents a drug type of a drug contained within the drug delivery device. The drug may be contained within the drug reservoir of the drug delivery device. Additionally or alternatively, a location of the at least one sensor may be representative of a drug type of a drug contained within the drug delivery device.

According to an embodiment, when a drug reservoir is inserted into the medical delivery device that is intended for use with that medical delivery device, the at least one sensor aligns with the at least one coding feature.

According to an embodiment, the at least one sensor comprises a capacitive sensor. A surface of the at least one coding feature and a surface of the at least one sensor may combine to form a capacitor.

According to an embodiment, the at least one coding feature comprises a mechanical feature. The mechanical feature can be distinguished by a user of the medical delivery device and by the at least one sensor.

A further aspect relates to a method of determining information related to a drug reservoir. The method may comprise at least one electronic sensor identifying a coding feature of a drug reservoir inserted in the medical delivery device. The method may further comprise a decoding module determining information related to the drug reservoir based on the identified coding feature.

According to an embodiment, the at least electronic sensor identifies the coding feature as the drug reservoir is inserted into the drug delivery device.

According to an embodiment, the method further comprises detecting a reading error. The method may further comprise alerting a user of the reading error.

According to an embodiment, the method further comprises controlling the speed of insertion of the drug reservoir into the medical delivery device.

Controlling the speed of insertion may comprise at least one of forcing the drug reservoir to travel along a non-axial path, a spring force controlling the speed of insertion, a frictional force controlling the speed of insertion, and a motor controlling the insertion.

According to a preferred embodiment, a medical delivery device is provided comprising at least one electronic sensor and a decoding module, wherein the at least one electronic sensor and the decoding module are configured to identify a coding feature of a drug reservoir inserted in the medical delivery device and to determine information related to the drug reservoir based on the identified coding feature.

According to a preferred embodiment, a medical delivery device is provided comprising at least one electronic sensor and a decoding module, wherein the at least one electronic sensor and the decoding module are configured to (i) identify a coding feature of a drug reservoir inserted in the medical delivery device and (ii) determine information related to the drug reservoir based on the identified coding feature.

According to a preferred embodiment, a medical delivery device is provided comprising a drug reservoir configured to be at least partially inserted into the medical delivery device, at least one coding feature provided on the drug reservoir and at least one electronic sensor configured to identify the at least one coding feature.

According to a preferred embodiment, a method of determining information related to a drug reservoir for a medical delivery device is provided, the method comprising at least one electronic sensor identifying a coding feature of the drug reservoir inserted in the medical delivery device and a decoding module determining information related to the drug reservoir based on the identified coding feature.

According to a preferred embodiment, a method of determining information related to a drug reservoir is provided, the method comprising at least one electronic sensor identifying a coding feature of a drug reservoir inserted in the medical delivery device and a decoding module determining information related to the drug reservoir based on the identified coding feature.

These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which:

FIG. 4A illustrates a perspective view of a reservoir inserted in a drug delivery device having a reservoir-identification system;

FIG. 4B illustrates a detailed view of the coding feature and reservoir-identification system of FIG. 4A;

FIG. 5A illustrates a perspective view of a reservoir inserted in a drug delivery device having a reservoir-identification system;

FIG. 5B illustrates a detailed view of the coding feature and reservoir-identification system of FIG. 5A;

DETAILED DESCRIPTION

The method and system of the present disclosure may allow for identifying information related to a drug reservoir by an electronic sensor. The proposed system and method may help a user to distinguish between medicament reservoirs, thereby ensuring that a medical delivery device can only be used with a medicament reservoir for which it is intended. In an arrangement, a given drug delivery device may be intended to only be used with a single drug reservoir. Thus, the proposed system and method may help a user to ensure that only the single given drug reservoir is used with the given drug delivery device. However, in other arrangements, a given drug delivery device may be intended for use with multiple drug reservoirs. Thus, the proposed system and method may help a user to ensure that only the intended reservoirs are used with the drug delivery device.

In addition to allowing a user to identify whether a given drug reservoir is intended to be used with a drug delivery device, the proposed system and method may also inform a user (or, more generally, any individual dealing with drug reservoirs in any capacity, such as manufacture, shipping, storage, etc.) of other useful information regarding a drug reservoir, such as required storage conditions for the reservoir and/or expiration date of the reservoir. In accordance with the present disclosure, information regarding a drug reservoir may be determined by determining information related to the drug reservoir based on an identified coding feature by using an electronic sensor and a decoding apparatus, for example. The method and system for identifying information related to the drug reservoir are described in greater detail below in the following subsections.

In accordance with the present disclosure, a medical delivery device may include a system configured to identify information about a drug reservoir inserted in the medical delivery device or drug delivery device. Such a system for determining information related to the drug reservoir may be provided on or in a drug delivery device, such as syringes, pen-type injection syringes, credit-card-shaped injection devices, electro-mechanical devices, pumps, inhalers, or other similar injection or infusing devices that require at least one reservoir containing at least one medicament. For example, such a system may be provided in drug delivery device 100 shown in FIG. 1A.

Figure 1A:
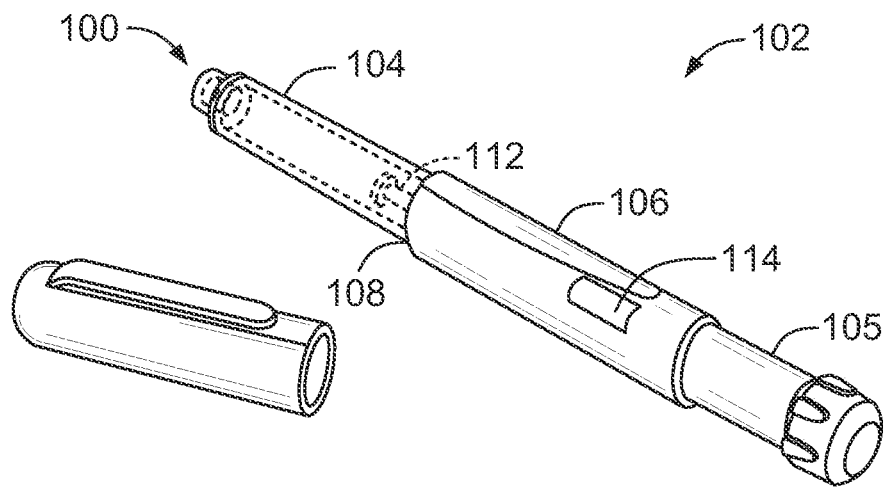
FIG. 1A illustrates a typical pen type drug delivery device that may include an embodiment of a reservoir-identification system.

Referring to FIG. 1A, there is shown the drug delivery device 100. The drug delivery device 100 comprises a housing 102 having a first reservoir retaining part 104, and second main (exterior) housing part 106. Housing part 106 may include a dose setting mechanism 105. A first end of the cartridge or reservoir retaining part 104 and a second end of the main housing 106 are secured together by retaining features 108. In this illustrated arrangement, the reservoir retaining part 104 is secured within the second end of the main housing 106. The pen type syringe may comprise a re-usable or a disposable pen type syringe. Where the syringe comprises a re-usable device, the cartridge holder or reservoir retaining part 104 and the dose setting mechanism 105 are removably coupled together. In a disposable device, they are permanently coupled together.

Figure 1B:
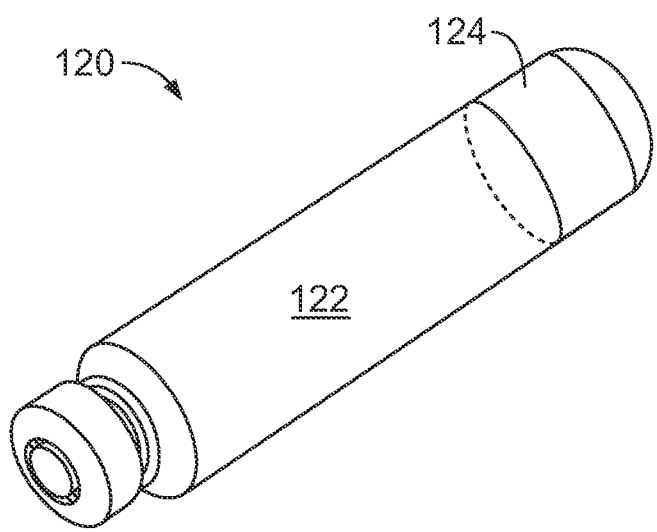
FIG. 1b, illustrates an example drug reservoir that may include a coding feature that may be detected by a reservoir-identification system.

A drug reservoir such as drug reservoir 120 shown in FIG. 1B, from which a number of doses of a medicinal product 122 may be dispensed, may be inserted in the cartridge retaining part 104. Preferably, the drug reservoir 120 contains a type of medicinal product or medicament 122 that must be administered often, such as once or more times a day. Once such medicament 122 is insulin.

The term "medicament", as used herein, preferably means a pharmaceutical formulation containing at least one pharmaceutically active compound, wherein in one embodiment the pharmaceutically active compound has a molecular weight up to 1500, Da and/or is a peptide, a protein, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3, or exedin-4, or an analogue or derivative of exedin-3, or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28, is replaced by Asp, Lys, Leu, Val or Ala and wherein in position B29, Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29, human insulin; B28-N-palmitoyl-LysB28ProB29 human insulin; B30-N-myristoyl-ThrB29LysB30, human insulin; B30-N-palmitoyl-ThrB29LysB30, human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta¬ decanoyl) human insulin.

Exendin-4, for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4, derivatives are for example selected from the following list of compounds:

H-(Lys)4-des Pro36, des Pro37, Exendin-4(1-39)-NH2,
H-(Lys)5-des Pro36, des Pro37, Exendin-4(1-39)-NH2,
des Pro36, [Asp28] Exendin-4(1-39),
des Pro36, [IsoAsp28] Exendin-4(1-39),
des Pro36, [Met(O)14, Asp28] Exendin-4(1-39),
des Pro36, [Met(O)14, IsoAsp28] Exendin-4(1-39),
des Pro36, [Trp(O2)25, Asp28] Exendin-4(1-39),
des Pro36, [Trp(O2)25, IsoAsp28] Exendin-4(1-39),
des Pro36, [Met(O)14, Trp(O2)25, Asp28] Exendin-4(1-39),
des Pro36, [Met(O)14, Trp(O2)25, IsoAsp28] Exendin-4(1-39); or
des Pro36, [Asp28] Exendin-4(1-39),
des Pro36, [IsoAsp28] Exendin-4(1-39),
des Pro36, [Met(O)14, Asp28] Exendin-4(1-39),
des Pro36, [Met(O)14, IsoAsp28] Exendin-4(1-39),
des Pro36, [Trp(O2)25, Asp28] Exendin-4(1-39),
des Pro36, [Trp(O2)25, IsoAsp28] Exendin-4(1-39),
des Pro36, [Met(O)14, Trp(O2)25, Asp28] Exendin-4(1-39),
des Pro36, [Met(O)14, Trp(O2)25, IsoAsp28] Exendin-4(1-39),
wherein the group -Lys6-NH2, may be bound to the C-terminus of the Exendin-4, derivative;
or an Exendin-4, derivative of the sequence
H-(Lys)6-des Pro36, [Asp28] Exendin-4(1-39)-Lys6-NH2,
des Asp28, Pro36, Pro37, Pro38Exendin-4(1-39)-NH2,
H-(Lys)6-des Pro36, Pro38, [Asp28] Exendin-4(1-39)-NH2,
H-Asn-(Glu)5des Pro36, Pro37, Pro38, [Asp28] Exendin-4(1-39)-NH2,
des Pro36, Pro37, Pro38, [Asp28] Exendin-4(1-39)-(Lys)6-NH2,
H-(Lys)6-des Pro36, Pro37, Pro38, [Asp28] Exendin-4(1-39)-(Lys)6-NH2,
H-Asn-(Glu)5-des Pro36, Pro37, Pro38, [Asp28] Exendin-4(1-39)-(Lys)6-NH2,
H-(Lys)6-des Pro36, [Trp(O2)25, Asp28] Exendin-4(1-39)-Lys6-NH2,
H-des Asp28, Pro36, Pro37, Pro38, [Trp(O2)25] Exendin-4(1-39)-NH2,
H-(Lys)6-des Pro36, Pro37, Pro38, [Trp(O2)25, Asp28] Exendin-4(1-39)-NH2,
H-Asn-(Glu)5-des Pro36, Pro37, Pro38, [Trp(O2)25, Asp28] Exendin-4(1-39)-NH2,
des Pro36, Pro37, Pro38, [Trp(O2)25, Asp28] Exendin-4(1-39)-(Lys)6-NH2,
H-(Lys)6-des Pro36, Pro37, Pro38, [Trp(O2)25, Asp28] Exendin-4(1-39)-(Lys)6-NH2,
H-Asn-(Glu)5-des Pro36, Pro37, Pro38, [Trp(O2)25, Asp28] Exendin-4(1-39)-(Lys)6-NH2,
H-(Lys)6-des Pro36, [Met(O)14, Asp28] Exendin-4(1-39)-Lys6-NH2,
des Met(O)14, Asp28, Pro36, Pro37, Pro38, Exendin-4(1-39)-NH2,
H-(Lys)6-desPro36, Pro37, Pro38, [Met(O)14, Asp28] Exendin-4(1-39)-NH2,
H-Asn-(Glu)5-des Pro36, Pro37, Pro38, [Met(O)14, Asp28] Exendin-4(1-39)-NH2,
des Pro36, Pro37, Pro38, [Met(O)14, Asp28] Exendin-4(1-39)-(Lys)6-NH2,
H-(Lys)6-des Pro36, Pro37, Pro38, [Met(O)14, Asp28] Exendin-4(1-39)-(Lys)6-NH2,
H-Asn-(Glu)5, des Pro36, Pro37, Pro38, [Met(O)14, Asp28] Exendin-4(1-39)-(Lys)6-NH2,
H-Lys6-des Pro36, [Met(O)14, Trp(O2)25, Asp28] Exendin-4(1-39)-Lys6-NH2,
H-des Asp28, Pro36, Pro37, Pro38, [Met(O)14, Trp(O2)25] Exendin-4(1-39)-NH2,
H-(Lys)6-des Pro36, Pro37, Pro38, [Met(O)14, Asp28] Exendin-4(1-39)-NH2,
H-Asn-(Glu)5-des Pro36, Pro37, Pro38, [Met(O)14, Trp(O2)25, Asp28] Exendin-4(1-39)-NH2,
des Pro36, Pro37, Pro38, [Met(O)14, Trp(O2)25, Asp28] Exendin-4(1-39)-(Lys)6-NH2,
H-(Lys)6-des Pro36, Pro37, Pro38, [Met(O)14, Trp(O2)25, Asp28] Exendin-4(S1-39)-(Lys)6-NH2,
H-Asn-(Glu)5-des Pro36, Pro37, Pro38, [Met(O)14, Trp(O2)25, Asp28] Exendin-4(1-39)-(Lys)6-NH2;
or a pharmaceutically acceptable salt or solvate of any one of the afore-mentioned Exedin-4, derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1, to R4, independently of each other mean: hydrogen, an optionally substituted C1, C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985, and in Encyclopedia of Pharmaceutical Technology.

Pharmaceutically acceptable solvates are for example hydrates.

In an embodiment, a system for determining information about the drug reservoir 120 is provided at or near the interface between the cartridge retaining part 104 and the main housing part 106. Thus, when the drug reservoir 120 is inserted in the drug delivery device 100, the system may detect information related to the reservoir 120 being inserted. A system for determining information about the drug reservoir 120 (which may herein be referred to as a reservoir-identification system) in accordance with embodiments of the present disclosure includes at least one electronic sensor and a decoding module. It should be understood, however, that in addition to identifying the drug reservoir 120, the reservoir-identification system may determine other information related to the drug reservoir 120. Such an identification system is described in greater detail below with reference to FIGS. 2-11. In an example, the electronic sensor may comprise a decoding module. In another example, the electronic sensor may be communicatively linked to the decoding module. The at least one electronic sensor and the decoding module may be configured to identify a coding feature of a drug reservoir inserted in the medical delivery device and/or to determine information related to the drug reservoir based on the identified coding feature.

Figure 2:
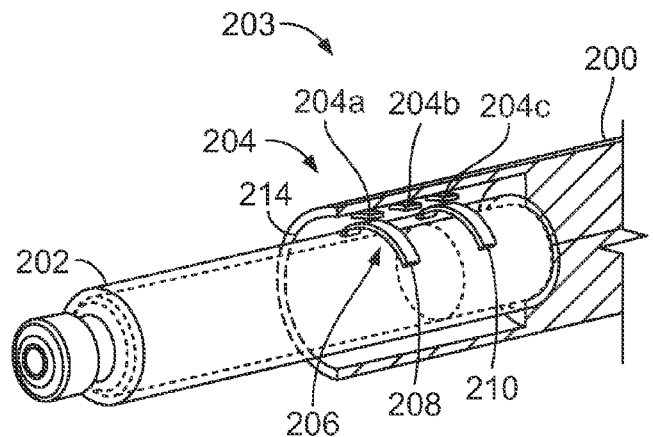
FIG. 2 illustrates a perspective view of a reservoir inserted in a drug delivery device having a reservoir-identification system.

FIG. 2 depicts a perspective view of a distal end of an example drug delivery device 200 that includes a reservoir-identification system 203. The system 203 may identify drug reservoir 202 when the reservoir 202 is inserted into the device 200. Drug delivery device 200 may be the same as or similar to drug delivery device 100 shown in FIG. 1. Reservoir-identification system 203 includes electronic sensors 204a, 204b, and 204c, which are configured to detect and identify a coding feature 206 of the drug reservoir 202. The sensors 204a, 204b, 204c, may include or may be coupled to a decoding module or decoding modules (not explicitly shown in FIG. 2). Sensors 204a-c, are depicted as being disposed on an inner wall 214 of a dose setting mechanism of the drug delivery device 200, however, they may be disposed elsewhere in or on the drug delivery device 200, such as an inner wall of a reservoir holder.

In this example, coding feature 206 is depicted as having two coding elements 208, 210. Each coding element 208, 210 may serve to identify separate information. Alternatively, the two coding elements 208, 210 together may serve to identify given information. Although coding feature 206 is depicted as being located on the proximal end of the drug reservoir 202, the coding feature 206 may be disposed at other locations. For example, the coding feature 206 may be on the reservoir, ferrule, bung, label, connector or an adaptor. However, in other given embodiments, the coding feature 206 may be disposed elsewhere, such as on the box of the drug reservoir 202 or drug reservoirs.

Figure 3:
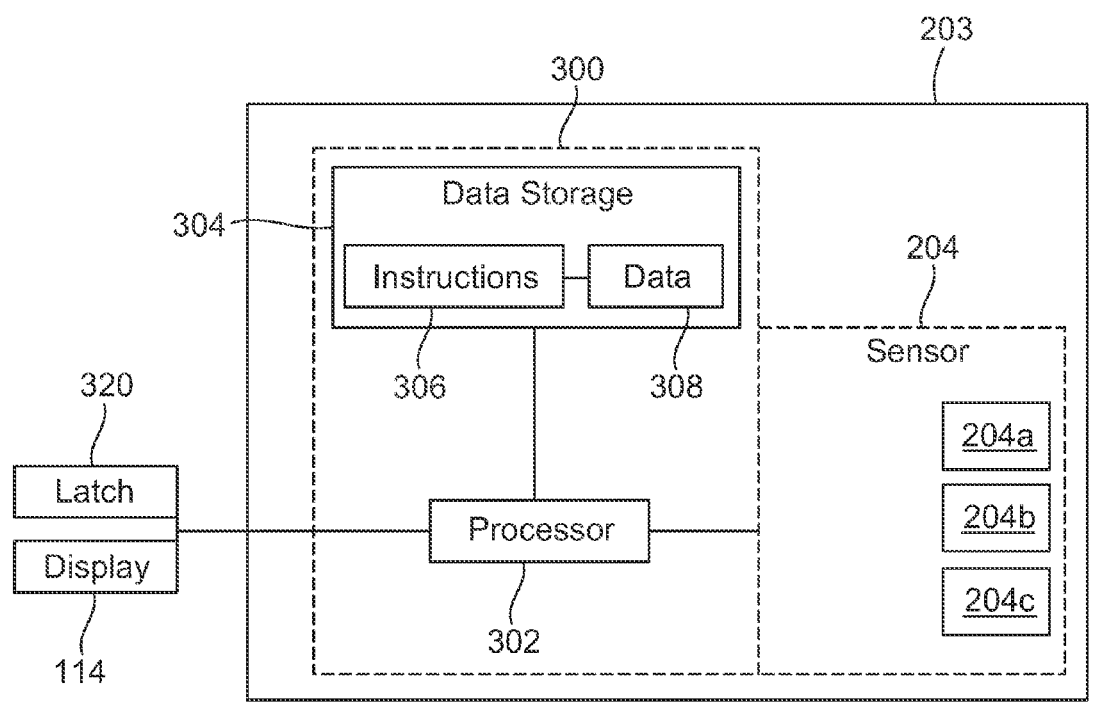
FIG. 3 illustrates an example reservoir-identification system.

Aspects of the reservoir-identification system 203 are depicted in greater detail in FIG. 3. As shown, the system 203 includes a sensor 204 that is coupled to a decoding module 300. In FIG. 3, sensor 204 is depicted as being communicatively linked to decoding module 300. However, it should be understood, that the sensor 204 (or sensors) itself may comprise the decoding module 300.

Decoding apparatus or module 300 includes a processor 302 and also includes data storage 304 comprising instructions 306 executable by the processor 302 to carry out the functions described herein. The processor 302 may comprise a single processor such as a general purpose microprocessor or multiple (e.g. parallel) processors. The data storage 304 may take various forms, in one or more parts, such as a non-volatile storage block and/or a removable storage medium, and may include the program instructions 306 executable by processor 302 for carrying out the system functions described herein. Data storage 304 may also include data 308, which may be used for carrying out the functions described herein.

The reservoir-identification system 203 is also depicted as being coupled to a latch 320 and display 114, as shown in FIG. 3. Display 114 may be located on an outer wall of the device 200, 100 in a place that is visually accessible to the user as can be seen from FIG. 1A. These elements may be used in given examples of the present disclosure for responding in some way to the identified drug reservoir inserted in the drug delivery device. Example ways of responding to the identified drug reservoir are described in greater detail below.

As mentioned above, the system 203 may operate to identify information related to a drug reservoir. Specifically, system 203 may operate to identify information related to the drug reservoir by first identifying a coding feature, such as coding feature 206 disposed on drug reservoir 202. As described in greater detail below, the coding feature 206 can be applied to a reservoir such as a cartridge, vial, ampoule, pouch, primary pack, or container. This coding feature may serve to indicate information about the drug reservoir the coding feature is disposed on. In an example embodiment, coding feature 206 is disposed directly on the drug reservoir 202, as shown in FIG. 2.

The sensor 204 and decoding apparatus 300 may operate in conjunction with one another to identify the coding feature and to determine information related to the drug reservoir. This identification and determination may occur at various stages of the use of the drug delivery device. For example, the system 203 may identify the coding feature and determine information related to the reservoir before, during, or after a drug reservoir is inserted into a drug delivery device.

In accordance with the proposed method and system, the electronic sensor 204 may communicate with the coding feature 206 so as to identify the coding feature 206. Many different sensors and coding features in accordance with the disclosed concept are possible. Further, the type of sensor 204 used may depend on the type of coding feature the sensor 204 is configured to detect.

As an example of a type of sensor 204 in accordance with the disclosed concept, the sensor 204 may be an optical sensor. For instance, the optical sensor may be a photosensor (e.g. photodiode, phototransistor), a bar code scanner, or a laser (e.g. CD/optical storage technology). An optical sensor may be used to detect numerous types of coding features. For example, the coding features that may be detected by such a sensor may be protrusions, indentations, color, or marks with different translucency/texture.

In an example, the drug delivery device 200 may include a light source (not explicitly shown in FIG. 2) that may interact with the coding features and/or the electronic sensor 204 in order to facilitate the determination of information related to the drug reservoir 202. When a light source is used to facilitate the determination of information, the coding feature may be located in the path between the light source and the sensor 204 and the coding feature may be used to guide or block light. FIGS. 4-5 depict example drug delivery devices that include a light source.

In FIG. 4A, a drug delivery device 400 includes a sensor 402 and a light source 404. A drug reservoir 406 includes a coding feature 408 that includes a guide path 410 (see FIG. 4B) created by an indentation in the coding feature 408. In this example, the sensor 402 is depicted as being arranged 180 degrees from the light source 404. However any number of degrees is possible. When the reservoir 406 is inserted into the drug delivery device 400, the coding feature guide path 410 may align with both the light source 404 and the sensor 402, and the guide path 410 guides light from the source 404 toward the sensor 402.

FIG. 4B depicts a close-up view of this arrangement. As can be seen, light from light source 404 can travel through the guide path 410 to the sensor 402. It should be appreciated that the sensor 402, light source 204, and coding feature 408 can be arranged in ways that may distinguish a large number of drug reservoirs 406. For instance, if the drug reservoir 406 is not intended for the drug delivery device 400, the coding feature 408 may be arranged so that the guide path 410 of the coding feature 408 does not align with the light source 404 and the sensor 402. In addition to alignment, the coding feature 408 may provide further coding or information about the reservoir 406 by manipulating the light in a given way. For example, the coding feature 408 may filter the light, change the polarization, cause a frequency shift, or manipulate the light in other ways. Given manipulations (e.g. a given polarization change, frequency change, etc.) may serve to indicate information about the particular drug reservoir 406.

FIGS. 5A-B depict another example arrangement of a drug delivery device that includes a light source in addition to the sensor and decoding apparatus. In FIG. 5A, drug delivery device 500 includes a sensor 502 and a light source 504. A drug reservoir 506 includes a coding feature 508, which includes indentations 510 and 512. In this example, the sensor 502 is adjacent to the light source 504, and the sensor 502 and the light source 504 are separated from one another by a slight gap 514 (see FIG. 5B). A similar sensor 502 and light source 504 may be aligned with indentation 510. In the arrangement of FIG. 5, the coding feature 508 may be configured to manipulate light from the light source 504 in some way, such as blocking the light entirely, allowing the light to pass through, allowing some of the light to pass through, or modifying the light in some other way. This specific example depicts indentation 512 aligning with the gap 514 and, therefore, light from light source 504 is able to travel to sensor 502 through gap 514. As mentioned above with respect to FIGS. 4A-B, the sensor 502, the light source 504, and the coding feature 508 can be arranged in ways that may distinguish a large number of drug reservoirs 506. For example, the coding feature 508 can be arranged to block light if the drug reservoir 506 is not intended for use with the drug delivery device 500. Hence, if no light is detected, the sensor 502 and the decoding apparatus may conclude that the coding feature 508 is an incorrect coding feature and, thus, the drug reservoir 506 is not intended for use with drug delivery device 500.

As another example of the type of sensor that may be included in a reservoir-identification system in accordance with the present disclosure, the sensor 204 may be a capacitive sensor. A capacitive sensor may detect capacitance due to protrusions and/or indentations (e.g. as in fingerprint-recognition technology). A capacitive sensor in accordance with the present disclosure may be any capacitive sensor known in the art or later developed. When coding features contact (or approach) the sensor, a capacitor can be formed between each electrode of the sensor and the corresponding surface of the coding features. Protrusions and indentations on the coding features would cause capacitance to vary, and by measuring discharge voltages across each capacitor, an image of the coding feature can be determined, in 2D or 3D. The decoding module or 300 may then analyze the image to determine information related to the drug reservoir.

As still yet another example, the sensor 204 may be a Hall sensor. In this case, the Hall sensor may read properties of a magnet that is disposed in or on a coding feature. A Hall sensor in accordance with the present disclosure may be any Hall sensor known in the art or later developed. As still yet another example, the sensor 204 may be an electro-mechanical switch operated when it contacts protrusions/indentations, e.g. a micro switch.

Figure 6A:
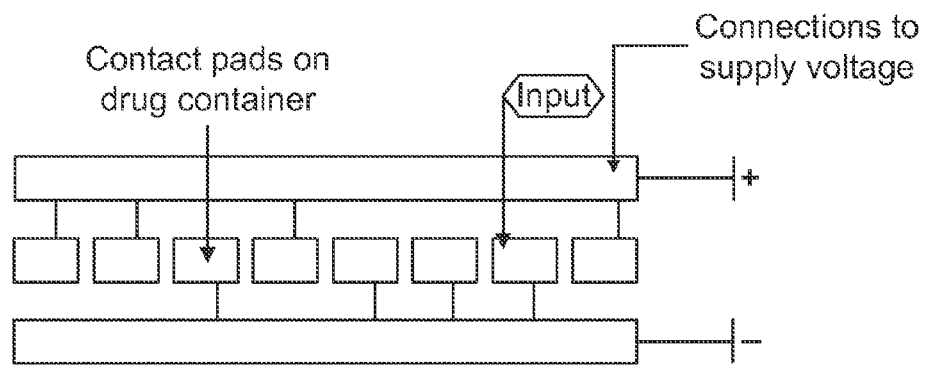
FIG. 6A illustrates an example connection between a sensor and a coding feature.

As still yet another example, the sensor 204 may be electrical contact pads each connected to known voltage levels (e.g. + or −voltage) within the drug delivery device, and with a contact on the drug delivery device to read the voltage at each pad. Between each pad, the container base material would be nominally zero voltage. FIG. 6A shows an example where only one pad is connected as an input to a decoding circuit, but there may be an input for each pad. This example depicted has eight contacts, which provides for 256, different combinations that may each identify a different drug reservoir or property of a drug reservoir.

Figure 6B:
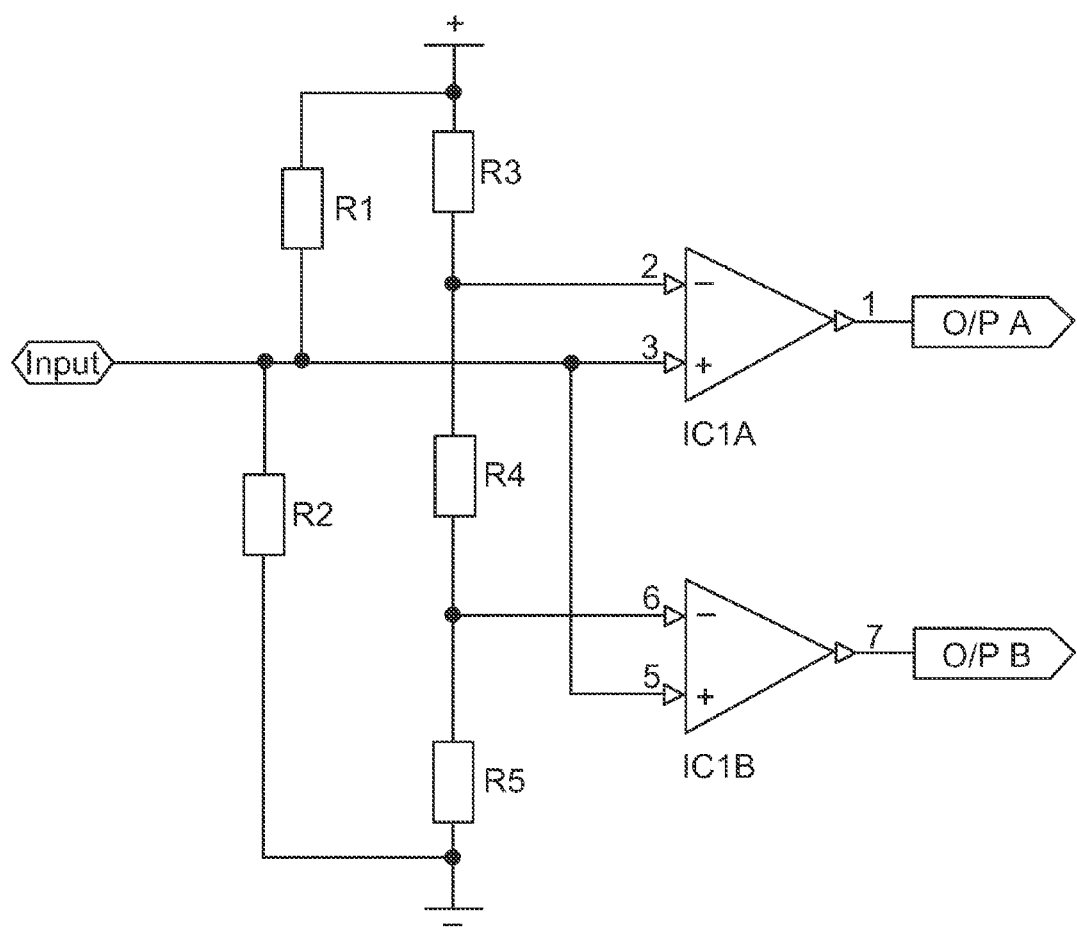
FIG. 6B illustrates an example decoding circuit.

FIG. 6B depicts an example decoding circuit of a decoding module 300 that may be used to decode the input from FIG. 6A. The example decoding circuit in FIG. 6B uses two comparators. If the input is connected to + then both outputs are high. If connected to −, both are low. If not connected, then output A is low and output B is high. An additional decoding circuit may be connected to each of the contact pads in FIG. 6A and the outputs could be read by processor 302, which may be a micro-controller.

As still yet another example, the sensor 204 may comprise electrical contact pads with a different electrical circuit between each pair. In such a case, the properties of each circuit can be read (e.g. resistance, capacitance), and information related to the reservoir can be determined based on the determined properties.

Figure 7A:
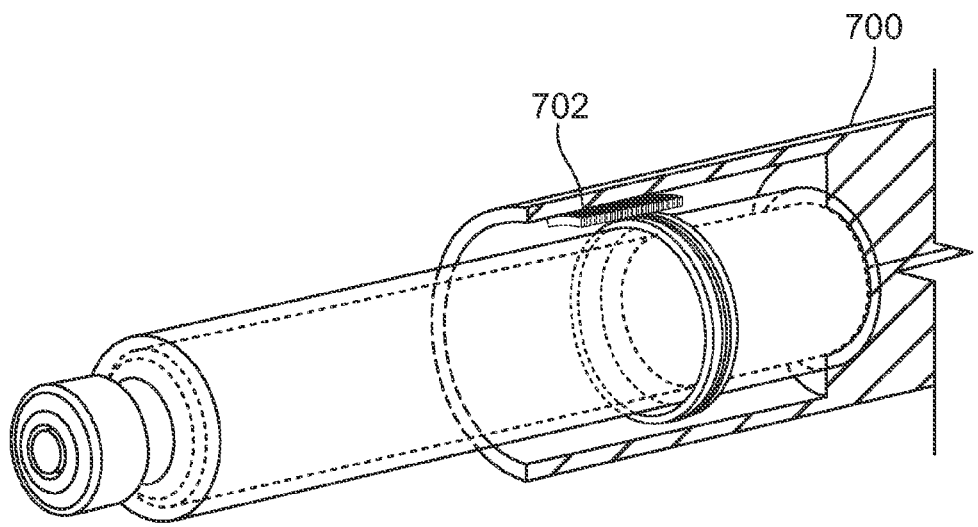
FIG. 7A illustrates a perspective view of a reservoir inserted in a drug delivery device having a reservoir-identification system.
Figure 7B:
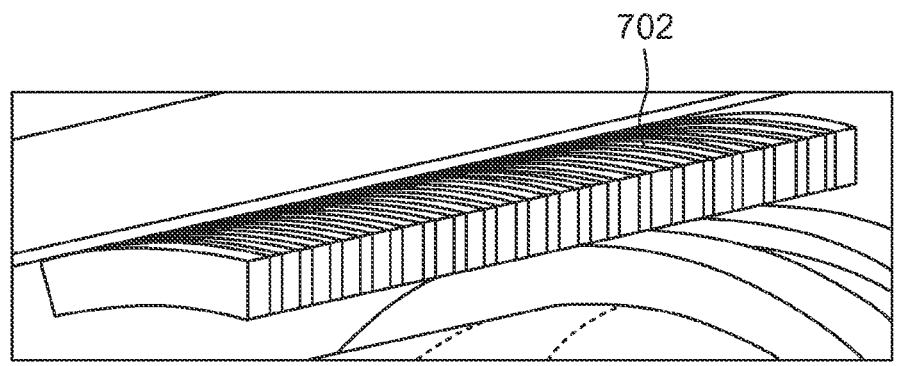
FIG. 7B illustrates a detailed view of the sensor of FIG. 7A.

In another embodiment, the sensor 204 may comprise an array of small sensors. For example, FIG. 7A depicts a drug delivery device 700 that includes a 'zebra strip' sensor 702. Such an array of small sensors would allow detection of any configuration of coding features. Each strip within the sensor 702 may detect the presence of a portion of any coding feature that is in its proximity, so the zebra strip sensor 702 can form an 'image' of the coding feature, and the size and relative position of each coding feature can be detected. As long as the zebra strip sensor 702 overlaps the coding features, it can detect the coding, and so it is less sensitive to geometric tolerances, or misalignment between the coding features and the sensors than other systems. A zebra strip sensor 702 could be used with any of the sensor technologies discussed above. A zebra strip sensor 702 in accordance with the present disclosure may be any zebra strip sensor known in the art or later developed.

In an embodiment, each coding element of the coding feature disposed on the reservoir may be read by a single sensor. Alternatively, each coding element could be read by more than one sensor, which may beneficially allow for error checking. Reading by multiple sensors may provide a layer of error-checking should one of the sensors be broken or not operating properly. In another embodiment of the present disclosure, each sensor element of the sensor could be aligned with a respective coding element. In such a case, only one sensor would be needed for each coding feature. However, it should be understood that a sensor may read multiple coding elements.

In an embodiment, a unique code on one or more of the sensors could confirm complete insertion of the reservoir before reading of the coding elements. For example, a system can be configured to read the coding elements after a signal on the most proximal sensor was detected, which may serve to indicate that the reservoir is fully inserted.

In addition to the types of sensors varying in examples of the present disclosure, the coding feature 206 detected by the sensor 204 may also vary. For example, as mentioned above, the coding features 206 that may be detected by such a sensor 204 may comprise protrusions, indentations, color, or marks with different translucency/texture. Other example coding features 206 are possible as well. Beneficially, different coding elements having different properties may each identify different drug reservoirs or different information about a given drug reservoir or reservoirs.

Aside from the physical differences of coding elements of the coding feature, coding of the reservoirs and information related to the reservoirs may be achieved in various other ways as well. In accordance with the proposed method and system, a large amount of information may be coded (e.g. distinguishing a large number of medicament reservoirs) by varying the coding feature disposed on the drug reservoir. For instance, multiple materials may be provided on a drug reservoir in order to provide coding for drug reservoirs. For example, a coding feature having three coded elements each serving to identify a unique piece of information related to the drug reservoir may be provided. Alternatively, the three coded elements may serve to together indicate a piece of information related to the reservoir.

Figure 9:
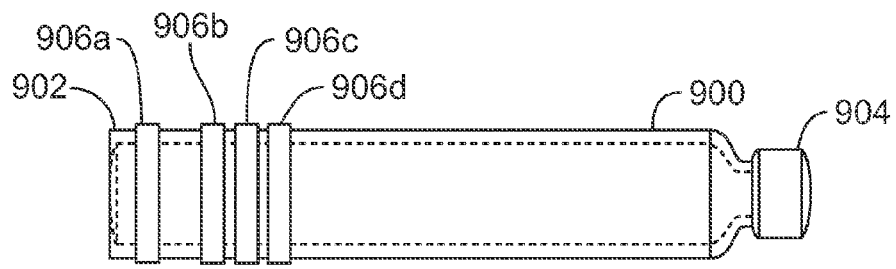
FIG. 9 illustrates an example coding feature.

The position of the coding feature 206 may also be used for identification purposes. For example, position of the coding feature 206 relative to a standard feature may be used to identify information about the drug reservoir. As such, the reservoir-identification system 203 may be further configured to detect the position of the coding feature 206. As an example, the axial length of the coding feature 206 from a proximal end of the reservoir may provide information related to the drug reservoir. FIG. 9 depicts a drug reservoir 900 having a proximal end 902 and a distal end 904. Reservoir 900 has coding elements 906a-d, disposed on the proximal end 902. The specific position of these coding elements 906a-d, relative to the proximal end 902 may represent information related to the drug reservoir 900. In an example, if r=4 coding elements 906a-d, can be located in n=9, possible positions, there are nCr=126, coding combinations. Accordingly, a large amount of information can be coded. It should be understood that the number of possible coding combinations could be increased by increasing the number of coding elements 906a-d, and the number of possible positions.

Figure 8:
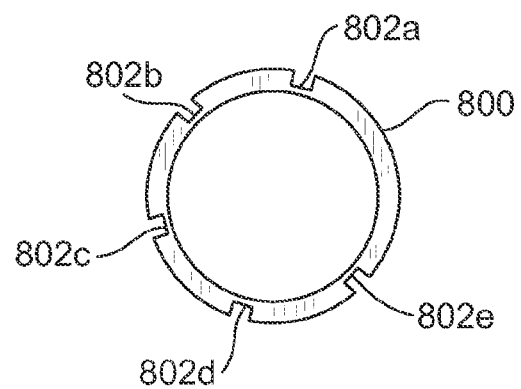
FIG. 8 illustrates an example coding feature.

In alternative embodiments, the system 203 may identify a coding feature based on the size (e.g. the axial, circumferential, and/or radial extent of the coding feature) or orientation (e.g. axial strips, circumferential rings, or 2D pattern) of the coding feature. For example, FIG. 8 shows a cross section of a coding feature 800 with indentations 802a-e, located around the circumference of the coding feature 800. The system 203 can determine information about where the drug reservoir coding feature 800 is disposed on based on the properties and location of the indentations 802a-e.

Figure 10A:
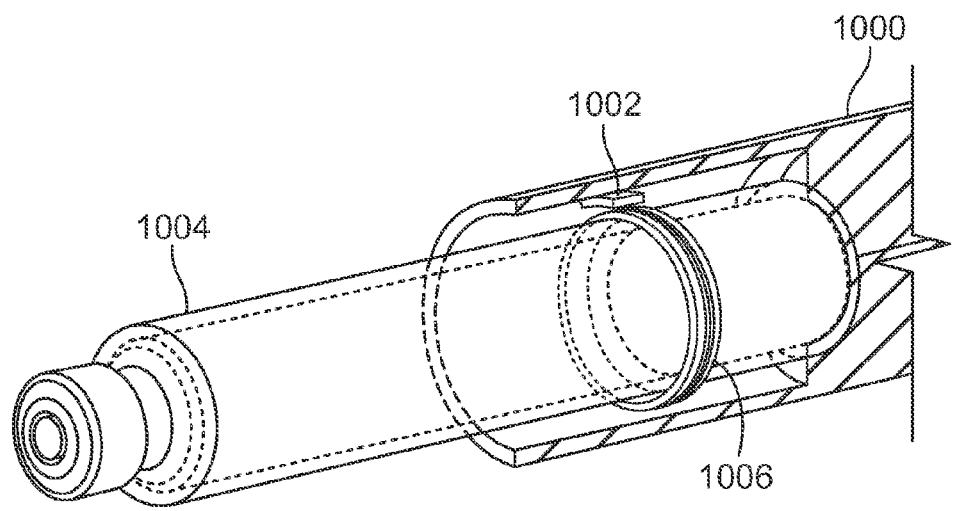
FIGS. 10A-D illustrates example coding features.
Figures 10B, 10C, 10D:
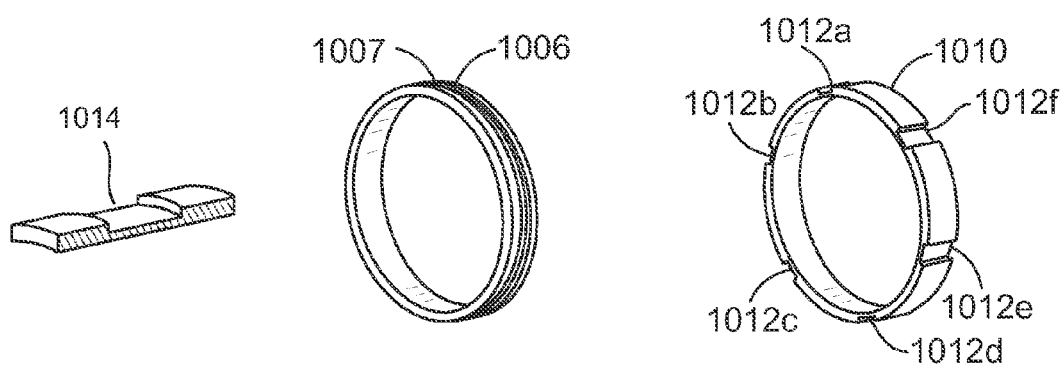

In an embodiment, the coding feature comprises a purely mechanical coding feature. The mechanical coding feature may be located, for example, on the sidewall of the drug reservoir, and may serve to indicate information about the reservoir, such as the drug type. FIGS. 10A and 10B depict example mechanical coding features.

FIG. 10A shows a drug delivery device 1000 that includes sensor 1002, where the sensor 1002 is configured to detect mechanical features. Drug reservoir 1004 has a mechanical coding feature 1006 disposed on it. FIG. 10C depicts coding feature 1006 in closer detail. Coding feature 1006 has an indentation 1007 that extends across the entire circumference of coding feature 1006. Sensor 1002 may detect this indentation 1007 and/or properties of this indentation 1007 (e.g. width, depth, position) when the reservoir 1004 is inserted in drug delivery device 1000.

The coding may be due purely to geometric features. However, as discussed above, the coding feature 1006 may incorporate additional coding elements, such as a magnet or a circuit. Each coding element may be a protrusion or an indentation around the circumference. For instance, FIG. 10D depicts a mechanical coding feature 1010 that has a plurality of indentations 1012a-f, around the circumference, and FIG. 10B depicts a mechanical coding feature 1014 that is a strip with a plurality of protrusions and/or indentations along its length.

In an embodiment, the coding feature may have elements that are sufficiently large and distinct from each other so that drug reservoirs can be distinguished from each other by a visually impaired user. Thus, in addition to an electronic sensor detecting the coding feature, a user may recognize a reservoir as correct or incorrect based on the look of the coding feature.

Where multiple coding features are used, each may be applied separately to the drug reservoir. Alternatively, a single coding feature may have a plurality of coding elements. For instance, one adaptor ring may have several coding rings formed on it.

Based on the identified coding feature, the system 203 may then determine information related to the drug reservoir. For instance, a given coding feature may be associated with given information. For example, the coding feature may vary for different types of drug reservoirs, and various coding features or coding feature properties may be associated with various information related to drug reservoirs. As a particular example, a first given coding feature may be associated with a first drug reservoir. A second given coding feature may be associated with a second drug reservoir. Further, a third coding feature may be associated with a third drug reservoir, and so forth.

As discussed above, system 203 may comprise data storage 304 that includes data 308. This data 308 may comprise a database of information that links a plurality of coding features or coding feature properties to respective information regarding a given drug reservoir. For example, the data 308 may include information that links a given coding feature or coding feature property to a type of drug the drug reservoir contains. In addition to identifying a type of drug or drug reservoir, the coding feature or properties of the coding feature may serve to identify other information about a drug reservoir. For example, the information related to the drug reservoir may be information related to the drug type, a drug concentration, a manufacturing date of the reservoir, an expiration date of the drug and a storage condition of the drug (e.g. required storage temperature). Other types of information about a drug reservoir are possible as well.

A method in accordance with the present disclosure comprises an electronic sensor and a decoding module identifying a coding feature of a drug reservoir inserted in the medical delivery device and then determining information related to the drug reservoir based on the identified coding feature. As mentioned above, the system 203 can read the coding feature at various times. For instance, in accordance with a method, the reservoir-identification system 203 can read the coding feature after the reservoir was inserted. Alternatively, the coding feature could be read during insertion. In this embodiment, the coding feature is read while the drug reservoir is being fitted to the device, so that only one small sensor may be needed.

Figure 11:
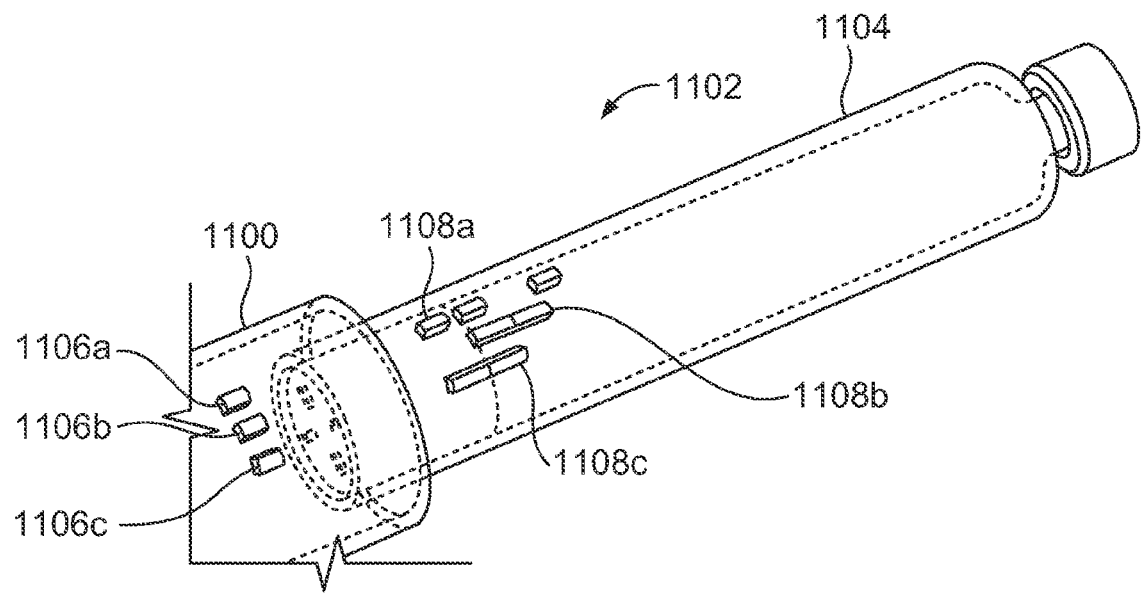
FIG. 11 illustrates a perspective view of a reservoir being inserted in a drug delivery device having a reservoir-identification system.

FIG. 11 depicts a drug delivery device 1100 that may read coding features 1102 on drug reservoir 1104 as it is being inserted into the device. Drug delivery device 1100 is depicted as including three sensors 1106a-c. Sensor 1106a, is configured to read row 1108a, of coding elements, sensor 1106b, is configured to read row 1108b, of coding elements, and sensor 1106c, is configured to read row 1108c. A single sensor 1106a-c, can read all the coding elements within a row 1108a-1108c, so fewer sensors 1106a-c, are needed than the number of coding elements.

Many of the sensing technologies discussed above may be applied. In some cases, some of the reading methods are more appropriate at high speed. Additional methods to read the code are possible due to motion. For example, magnetic strip induces voltage in reading head, e.g. tape recorder technology. This additional method is more appropriate at a high speed of insertion, typically appropriate for an insertion rate of 5, cm/s although it may be within or outside the range from 1, cm/s to 1, m/s as well.

In an embodiment, reading errors can be detected by the reservoir-identification system 203. By detecting reading errors, the user may be warned in such a case. This may beneficially prevent a user from assuming the drug reservoir is safe to use when it actually is not (e.g. if the system would have identified the reservoir as incorrect if not for the reading error).

In an embodiment of error detection in accordance with the present disclosure, the drug coding can be on one 'channel', and other channel(s) used to provide information on the position and/or direction of movement of the container. The position data may be a Gray code, which changes only one bit at a time, e.g. 1, bit (0 1 0, . . . ), 2, bit (00 01 11 10 00, . . . ), 3-bit (000 001 011 010, . . . ), or more bits. The position data can be repeated when finished, or more bits used to define a unique position. Alternatively, the position data may be a quadrature code where two (or more) rows of identical information are out of phase with each other, e.g. 0 1 0 1, . . . in the first row and 1 0 1 0, . . . in the second row. The drug coding itself can be repeated where two (or more) rows of identical coding are out of phase with each other.

For these error detection methods, the limits of data could be detected by a unique value at the start and/or end, e.g. 11, then 10 00 01 00 10, . . . , or mechanical features on the container could be detected. Further, the first value would preferably not be the same as the value that would be read if no coding is present, e.g. start with 01, instead of 00. Still further, preferably, data would be logged continuously during insertion so that each bit of the drug code and position code is read more than once. Then each bit of the drug code can be identified in a stable region, i.e. away from any positions where the position code is changing.

High or variable insertion speeds may cause logging errors or errors may be due to contacts bouncing. Problems can be reduced by controlling the insertion speed, e.g. the container is inserted along a non-axial path (possibly rotating on a helix or slope) or is inserted against a spring force or is slowed by friction or insertion is motorized. Accuracy may be improved if the speed of insertion is known or can be measured. The drug delivery device may therefore be configured to regulate the insertion speed. This may be done through a motorized insertion process. Alternatively, resistance caused by a spring force or friction may force a given insertion speed.

Each bit of code can be read once only, or more than one bit can be read simultaneously, which allows each bit to be read more than once and so, beneficially, allows error checking Since information regarding the drug reservoir may be detected during or after a drug reservoir is inserted into a drug delivery device, the reservoir-identification system 203 may react to the identified information at various stages in an operating sequence of a drug delivery device, such as drug delivery device 200. Specifically, system 203 may be configured to take certain actions when a drug reservoir is identified. For instance, the system 203 may react to the information and take an appropriate action during (i) loading of the device, (ii) dose selection, and (iii) dispensing of the drug. Other stages are possible as well. Beneficially, during these steps, the system 203 may help a user identify whether the drug reservoir being loaded or that is loaded is intended for the drug delivery device.

The step of determining information related to the drug reservoir may be performed as a user loads the drug reservoir 202 in drug delivery device 200. System 203 may identify coding feature 206 of the drug reservoir 202 and then may determine, based on the identified coding feature 206, whether the drug reservoir 202 is intended for use with the drug delivery device 200.

In an embodiment, when the drug reservoir is not intended for use with the drug delivery device 200, the system 203 may display an indication that the drug reservoir 20 is not intended for use with the drug delivery device 200. For instance, as shown in FIG. 3, the system 203 may comprise the display feature 114 that is in communication with the processor 302. This display feature 114 could indicate that the drug reservoir 202 is incorrect. For example, the display feature 114 may display a red dot or red "X" when an incorrect device 200 is loaded. The display feature 114 may also operate to indicate when a correct drug reservoir 202 is loaded. For example, the display feature 114 may display a green dot when a correct drug reservoir 202 is loaded. Other types of indications are possible as well, such as an audible indication.

If a user attempts to insert an incorrect reservoir 202 into the drug delivery device 200, the system 203 may operate to prevent the insertion of the drug reservoir 202 into the drug delivery device 200. For instance, preventing insertion of the drug reservoir 202 may comprise activating an electronically-controlled latch, such as latch 320 shown in FIG. 3, which prevents complete insertion of the drug reservoir 202. System 203 may also be configured to prevent the reset of a piston rod of the dose setting mechanism 105 of the drug delivery device 100 if the user attempts to load an incorrect drug container, such as piston rod 112 shown in FIG. 1A.

In an embodiment, system 203 may be configured to block the insertion of all drug reservoirs other than a given drug reservoir for which the drug delivery device is intended. In another embodiment, the system may be configured to only block drugs that are considered dangerous for using with the device (e.g. a short-acting drug could be fitted into a device intended for long-acting insulin, or a low-concentration drug could be fitted into a device intended for a high-concentration drug, but not vice versa).

The system 203 may also react to an identified drug reservoir and take an appropriate action during a dose selection phase (i.e. when a user is selecting a dose). For instance, system 203 may be configured to control dose selection based on the identified drug reservoir. Similar to preventing loading of an incorrect drug reservoir, system 203 may be configured to prevent dose selection when the identified drug reservoir is not intended for use with the drug delivery device. System 203 may, for instance, trigger a latch, such as latch 320, that prevents a user from setting a dose when an incorrect reservoir is loaded in the drug delivery device.

Other examples of controlling dose selection are possible as well. For instance, system 203 may control dose selection based on the identified drug reservoir by setting or enforcing a maximum dose. The drug reservoir may contain a drug that should only be dosed in small increments (e.g. 20 units or less). Thus, the system 203 may be configured to prevent a user from setting a dose greater than 20 units when such a drug reservoir is inserted in the drug delivery device. As another example, system 203 may control dose selection based on the identified drug reservoir by setting or enforcing a minimum dose.

As yet another example, system 203 may control dose selection based on the identified drug reservoir by controlling the dosing frequency. For instance, if a drug should not be dosed more than once a day, after a user injected a dose, the system 203 may be configured to lock the drug delivery dose setting mechanism out for a 24-hour period. For example, the system 203 may activate the electronic latch 320 to prevent dose setting for the 24-hour period.

The method and system 203 in accordance with the present disclosure may also react and take an appropriate action during the dispensing phase (i.e. when a user dispenses the drug). The system 203 may be configured to control dispensing of the drug based on the identified drug reservoir. For example, similar to preventing loading of an incorrect drug reservoir and dose selection with an incorrect reservoir, system 203 may be configured to prevent dispensing when the identified drug reservoir is not intended for use with the drug delivery device.

As another example, controlling dispensing of the drug based on the identified drug reservoir may include controlling a dispense speed and/or a required dispense force. Controlling a dispense speed and/or a required dispense force may be beneficial for various reasons. For example, certain drugs may require an increased dispense force due to crystallizing on the bung and/or high viscosity. In such a case, it may be beneficial to inject the drug slowly in order to reduce the force needed by a motorized drive. Further, in such a case, injecting such a drug may be painful for the user, so slower injection may reduce any pain. As another example, one other reason to control speed/force is to detect abuse loads, e.g. to detect blockages it is necessary to know what force is 'normal' for a given drug at a given speed.

As yet another example of identifying information related to a drug reservoir, system 203 may be used to identify the time that has elapsed since a drug reservoir was loaded into a drug delivery device. For example, the time at which the cartridge holder latch was last operated could be recorded into memory in the device, or on the drug reservoir.

System 203 may also be used as part of a 'closed loop' drug pump. The pump would detect the patient's needs, for example using a Blood Glucose Monitor, and then dispense the correct amount of drug, for example insulin. This system 203 may be able to vary the volume of drug dispensed to allow for variables such as drug concentration, or drug type.

Rather than system 203 being disposed in or on a drug delivery device, system 203 may be a stand-alone device, such as a scan gun or used for identifying information related to drug reservoirs or a drug-identification base station. The stand-alone system may be used by, for example, a patient or medical staff personnel, or a drug manufacturer in order to identify information related to drug reservoirs. Such a stand-alone device may be used for a variety of reasons. For example, the stand-alone system may be used to aid with storage or shipping of drug reservoirs. As a particular example, the system 203 may be used to identify the expiration date of the drug reservoir. As another example, system 203 may be used to identify required storage conditions for the drug reservoir. It may also be possible to record storage conditions experienced by a cartridge, e.g. with a temperature sensitive label, and for this information to be read by the device.

The method and system 203 of the present disclosure result in a number of advantages. For example, the method and system 203 result in a user-friendly system that identifies information related to a drug reservoir automatically by electronic means. More, there are quite a large number of different coding materials that may be used. Consequently, with the disclosed coding scheme, a large number of medicaments can be distinguished from one another. Moreover, with the disclosed coding scheme, if a user attempts to load an incorrect reservoir, the user may be alerted at an early stage of the assembly process that the user is attempting to load in incorrect reservoir, and hence attempting to possibly use a wrong medicament.

Additionally, the proposed system and method may make drug reservoirs difficult to counterfeit. The proposed system and method may beneficially reduce tampering and/or counterfeiting of drug reservoirs. Because such reservoirs with coding features may be difficult to tamper with, they may also reduce the risk of counterfeiting: i.e. making it more difficult for counterfeiters to provide unregulated counterfeit medicament carrying products.

In certain embodiments, an additional benefit is that no electrical contacts are needed. Another benefit is that the disclosed method and system provided a low-cost coding scheme for coding drug reservoirs and providing information about drug reservoirs. Further, in certain embodiments, sensitivity to geometric tolerances is reduced. Still further, in certain embodiments, the coding features are mechanical, so the coding features can be detected electronically as well as by the user.

Although aimed primarily at the insulin market, the present disclosure may apply to other drugs. The present disclosure may apply to various devices, including the following examples; an injector pen with a cartridge (e.g. 3, ml cylindrical glass cartridge) and a separate holder as illustrated in FIG. 1A. The present disclosure may also apply to an injector pen with a cartridge (e.g. 3, ml cylindrical glass cartridge) non removably retained in a holder, so that the holder will be disposed of with the primary pack, and to an injector pen where the primary pack attaches directly to the pen, e.g. an injection moulded polymer cartridge.

Figure 12:
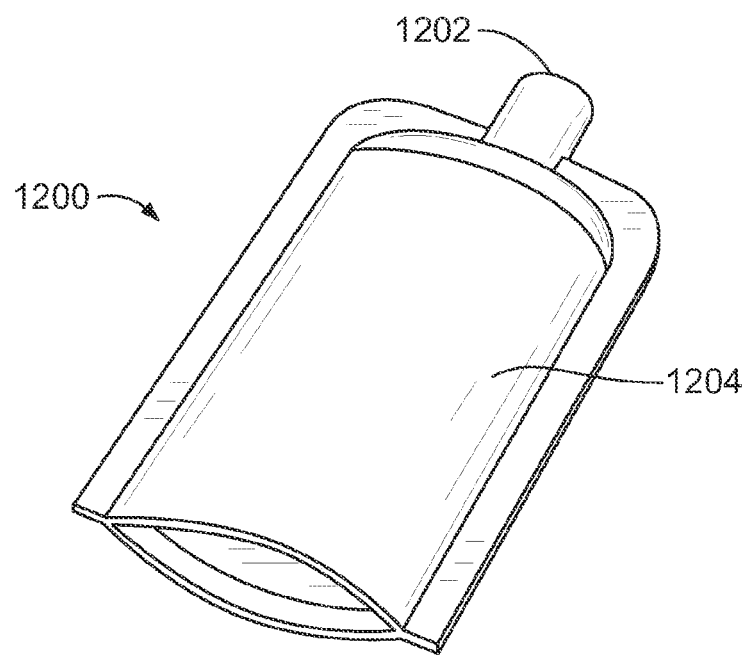
FIG. 12 illustrates an alternative reservoir that may be used in accordance with embodiments of the proposed system and method.

In other applications, the present disclosure may apply to any drug delivery device with any type of primary pack, e.g. inhaler, pouch. For example, coding features such as a coding feature may be added to a pouch, such as the pouch 1200 illustrated in FIG. 12. In an embodiment, coding features are added to port 1202. However, coding feature may also be added to the body 1204 of the pouch 1200.

Figure 13:
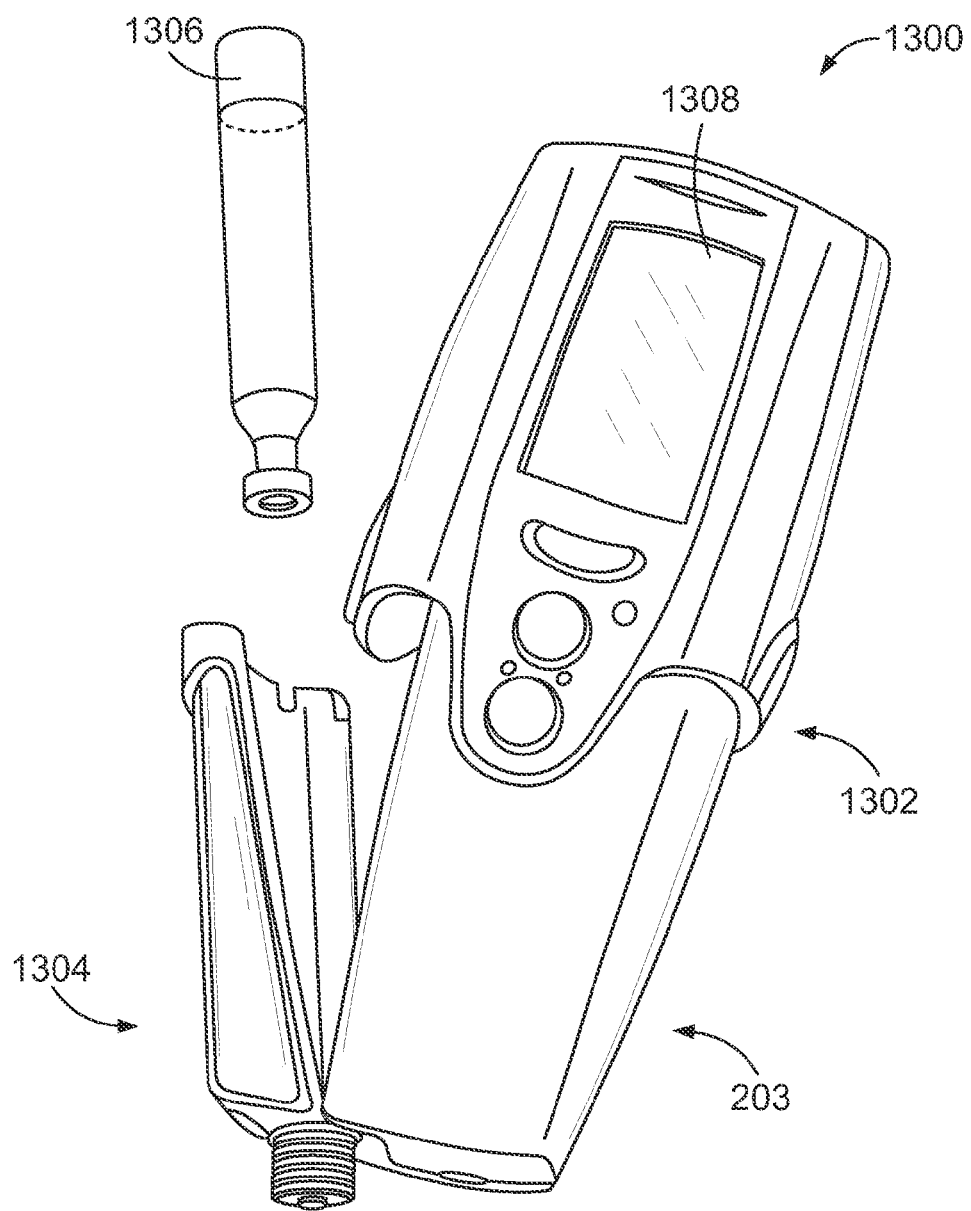
FIG. 13 illustrates another example drug delivery device that may include the reservoir-identification system of FIG. 3.

Another example of a device that may include system 203 is shown in FIG. 13. System 203 may be provided in drug delivery device 1300 shown in FIG. 13. Referring to FIG. 13, there is shown the drug delivery device 1300, which is a credit-card-shaped drug delivery device. Drug delivery device 1300 comprises a body 1302. Body 1302 includes a cartridge retaining portion 1304 into which a cartridge 1306 may be inserted. When cartridge 1306 is inserted, system 203 may detect information related to a coding feature of the cartridge 1306. Device 1300 also includes a screen 1308, which may display information related to the cartridge 1306 to the user of the device 1300. It should be understood that system 203 may be used in various other devices as well.

Exemplary embodiments of the present invention have been described. Those skilled in the art will understand, however, that changes and modifications may be made to these arrangements without departing from the true scope and spirit of the present invention, which is defined by the claims.

The invention claimed is:

1. A medical delivery device comprising:
    at least one electronic sensor and a decoding module, wherein the at least one electronic sensor and the decoding module are configured to
        (i) identify a coding feature of a drug reservoir inserted in the medical delivery device and
        (ii) to determine information related to the drug reservoir based on the identified coding feature,
    wherein the coding feature comprises at least one protrusion and/or indentation around a ring, wherein the ring wraps around the drug reservoir.

2. The medical delivery device of claim 1, comprising the drug reservoir, wherein the at least one coding feature is provided on the drug reservoir.

3. The medical delivery device of claim 1, wherein the electronic sensor comprises the decoding module.

4. The medical delivery device according to claim 1, wherein the decoding module comprises:
    a processor; and
    data storage comprising instructions executable by the processor to carry out the step of determining information related to the drug reservoir based on the identified coding feature.

5. The medical delivery device according to claim 1, further comprising:
    a drug reservoir holder and a dose setting mechanism, wherein the drug reservoir holder is capable of receiving the drug reservoir and the drug reservoir holder is attachable to the dose setting mechanism, and wherein the at least one electronic sensor is located on an inner wall of the drug reservoir holder or on an inner wall of the dose setting mechanism.

6. The medical delivery device according to claim 1, wherein the at least one electronic sensor comprises a sensor selected from the group consisting of an optical sensor, a photodiode, a scanner, a capacitive sensor, a Hall sensor, a zebra-strip sensor and/or an electrical contact.

7. The medical delivery device according to claim 1, wherein the coding feature comprises a plurality of coding elements, and wherein the at least one electronic sensor comprises a plurality of electronic sensors, wherein each electronic sensor of the plurality identifies a respective element of the coding feature.

8. The medical delivery device according to claim 1, wherein the coding feature is a coding feature selected from the group consisting of a bar code, a protrusion, an indentation, a color, a light-emitting coding feature, a magnet, and an electrical contact.

9. The medical delivery device according to claim 1, wherein the medical delivery device further comprises a light source, wherein light from the light source interacts with the sensor.

10. The medical delivery device of claim 9, wherein the coding feature guides light from the light source to the sensor.

11. The medical delivery device according to claim 1, wherein the coding feature is a mechanical coding feature, the mechanical coding feature comprising a plurality of geometric features, and wherein the mechanical coding feature can be distinguished by a user of the medical delivery device and by the at least one sensor.

12. The medical delivery device according to claim 1, wherein a location of the at least one coding feature and/or a location of the at least one sensor represents a drug type of a drug contained within the medical delivery device.

13. The medical delivery device according to claim 1, wherein, when a drug reservoir is inserted into the medical delivery device that is intended for use with that medical delivery device, the at least one sensor is configured to align with the at least one coding feature.

14. The medical delivery device according to claim 1, wherein a surface of the at least one coding feature and a surface of the at least one sensor combine to form a capacitor.

15. A method of determining information related to a drug reservoir for a medical delivery device, the method comprising:
    at least one electronic sensor identifying a coding feature of the drug reservoir inserted in the medical delivery device, where the at least one electronic sensor identifies the coding feature as the drug reservoir is inserted into the medical delivery device;
    a decoding module determining information related to the drug reservoir based on the identified coding feature; and
    controlling the speed of insertion of the drug reservoir into the medical delivery device, wherein controlling the speed of insertion comprises at least one of forcing the drug reservoir to travel along a non-axial path, a spring force controlling the speed of insertion, a frictional force controlling the speed of insertion, and a motor controlling the insertion.

16. The method of claim 15, further comprising the steps of detecting a reading error and alerting a user of the reading error.

* * * * *